(12) United States Patent
Harsy

(10) Patent No.: US 11,793,670 B2
(45) Date of Patent: Oct. 24, 2023

(54) COLD THERAPY DEVICE AND METHOD

(71) Applicant: Douglas R. Harsy, Southlake, TX (US)

(72) Inventor: Douglas R. Harsy, Southlake, TX (US)

(*) Notice: Subject to any disclaimer, the term of this patent is extended or adjusted under 35 U.S.C. 154(b) by 438 days.

(21) Appl. No.: 16/898,543

(22) Filed: Jun. 11, 2020

(65) Prior Publication Data

US 2021/0386579 A1 Dec. 16, 2021

(51) Int. Cl.
*A61F 7/00* (2006.01)

(52) U.S. Cl.
CPC .... *A61F 7/0085* (2013.01); *A61F 2007/0001* (2013.01); *A61F 2007/0056* (2013.01); *A61F 2007/0087* (2013.01); *A61F 2007/0096* (2013.01); *A61F 2007/0098* (2013.01)

(58) Field of Classification Search
None
See application file for complete search history.

(56) References Cited

U.S. PATENT DOCUMENTS

| | | |
|---|---|---|
| 2,726,658 A | 12/1955 | Chessy |
| 2,932,491 A | 4/1960 | Miller |
| 4,259,961 A | 4/1981 | Hood, III |
| 4,476,685 A | 10/1984 | Aid |
| 5,097,829 A | 3/1992 | Quisenberry |
| 5,174,285 A | 12/1992 | Fontenot |
| 5,671,808 A | 9/1997 | Kleyn |
| 5,730,720 A * | 3/1998 | Sites ............. G16H 20/40 604/27 |
| 5,865,841 A | 2/1999 | Kolen et al. |
| 6,277,143 B1 * | 8/2001 | Klatz ............. A61F 7/00 607/104 |
| 6,942,015 B1 | 9/2005 | Jenkins |
| 7,070,612 B1 | 7/2006 | Collins et al. |
| 7,204,041 B1 * | 4/2007 | Bailey, Sr. ......... A43B 7/06 36/1 |
| 7,959,657 B1 | 6/2011 | Harsy |
| 8,613,762 B2 | 12/2013 | Bledsoe |
| 9,566,187 B2 * | 2/2017 | Edelman ........... A61F 7/10 |
| 10,537,465 B2 | 1/2020 | Dabrowiak et al. |
| 2010/0292673 A1 * | 11/2010 | Korogi ............. A61M 39/20 604/533 |
| 2011/0238051 A1 * | 9/2011 | Levinson .......... A61F 7/02 606/22 |
| 2014/0350648 A1 * | 11/2014 | Ericson ............. A61M 16/04 607/105 |
| 2016/0354140 A1 * | 12/2016 | Sharma ............. A61B 18/04 |

* cited by examiner

*Primary Examiner* — Joanne M Rodden
*Assistant Examiner* — Nora W Rhodes
(74) *Attorney, Agent, or Firm* — Dan Brown Law Office; Daniel R. Brown

(57) ABSTRACT

A cold therapy apparatus includes a thermal body wrap with umbilical to a control unit with pump for circulating a thermal fluid to remove heat from a body. A coolant heat exchange assembly includes a coolant tank that is filled with a coolant and has a heat exchanger inside that is immersed in the coolant. The heat exchanger is coupled to the control unit to circulate the thermal fluid through the thermal body wrap. The coolant heat exchange assembly is removed from the control unit and placed in a cold environment to chill the coolant, and is then re-coupled during cold therapy. The process is repeated form extended therapy periods.

21 Claims, 14 Drawing Sheets

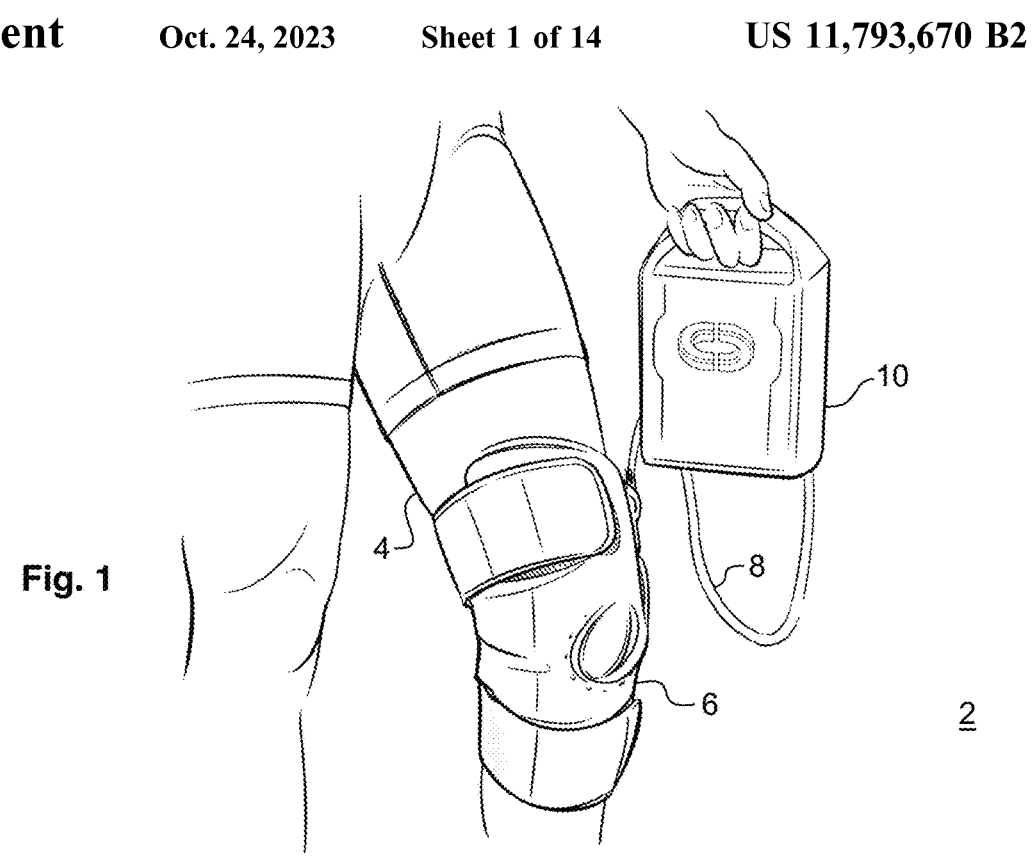
Fig. 1
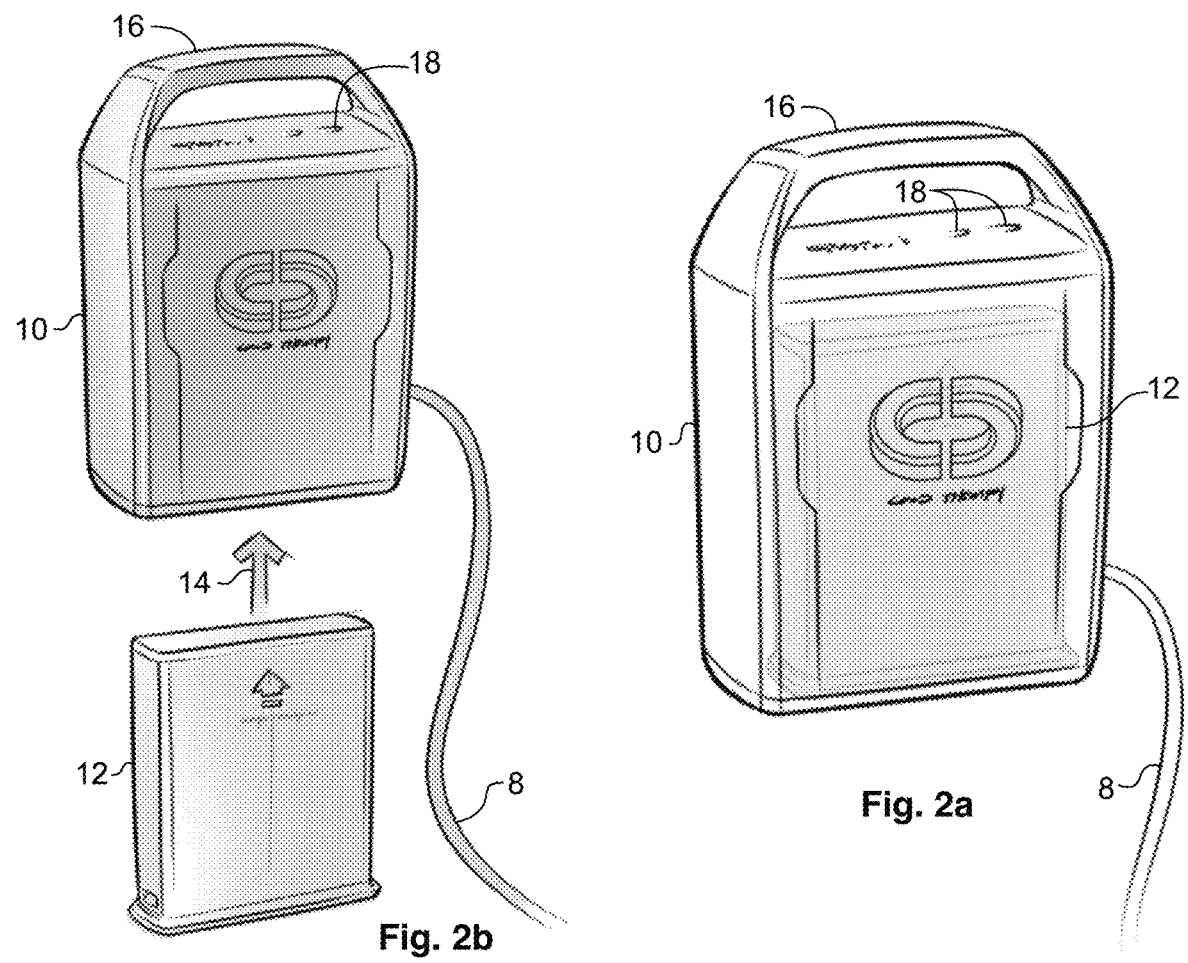
Fig. 2a
Fig. 2b

Section A-A
Exploded

Section B-B
Exploded

Section A-A

Section B-B

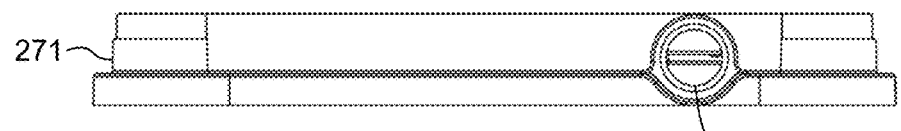
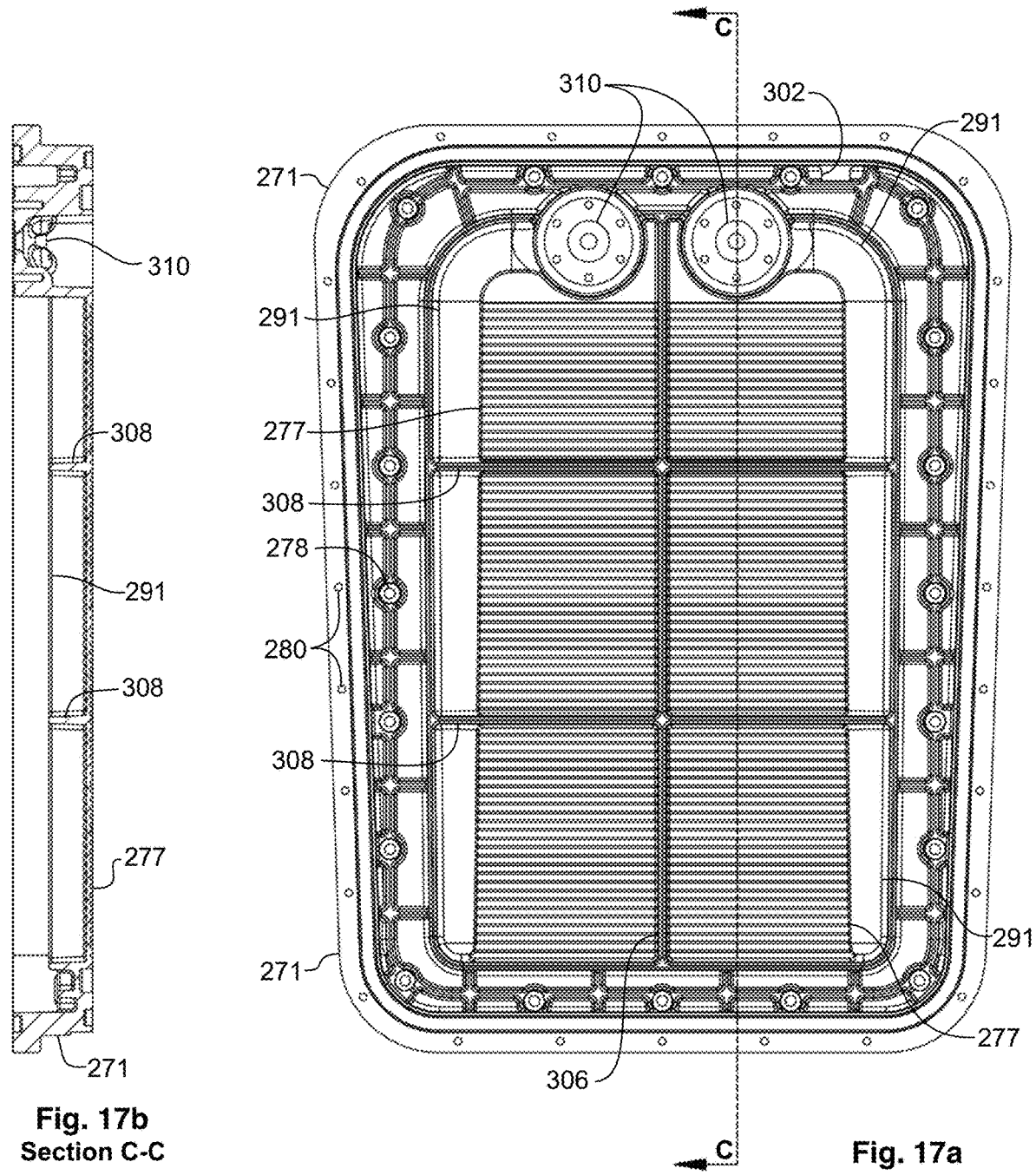
Fig. 17c
Fig. 17b
Section C-C
Fig. 17a

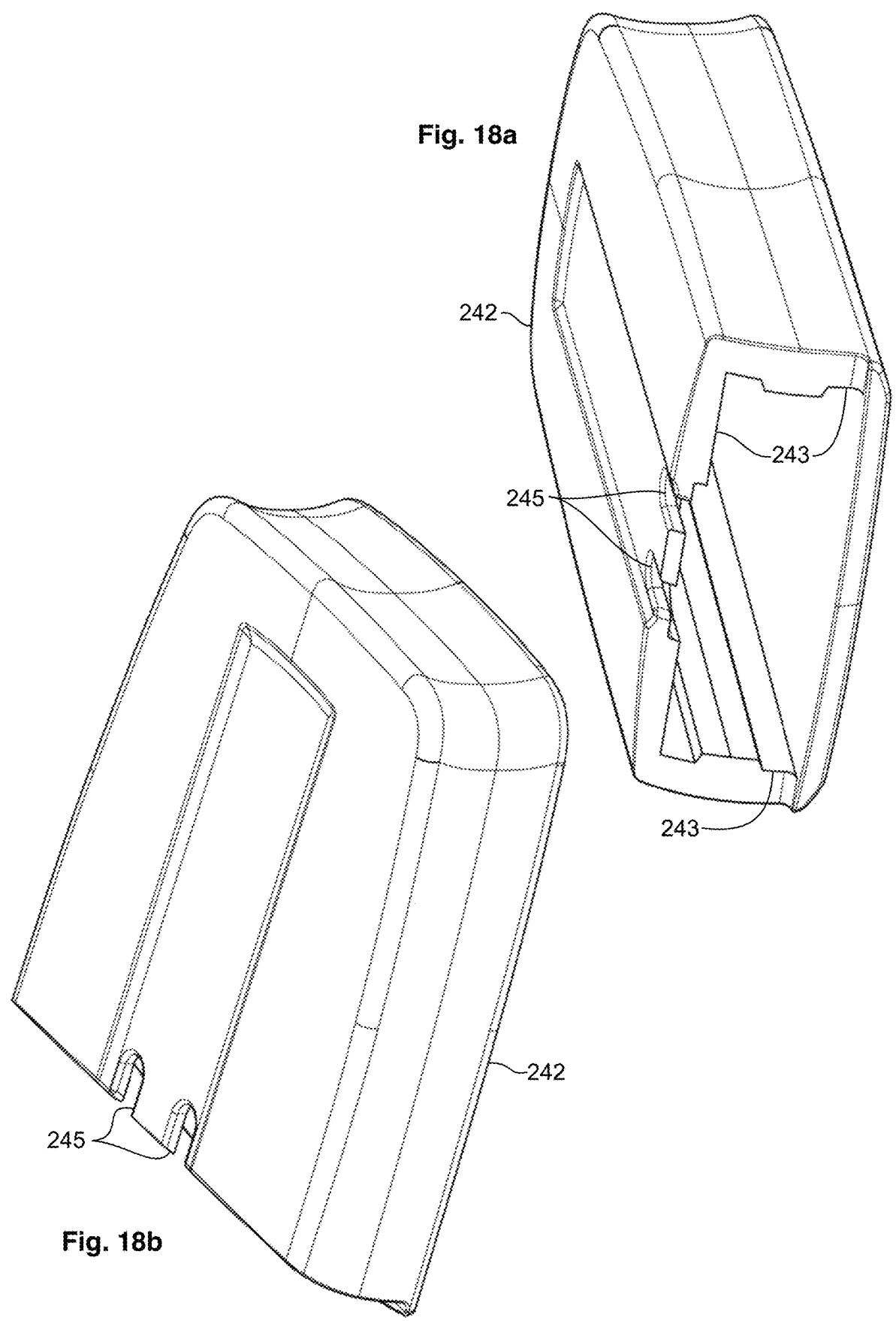

COLD THERAPY DEVICE AND METHOD

BACKGROUND OF THE INVENTION

Related Applications

None.

Field of the Invention

The present invention relates to cold therapy devices. More particularly, the present disclosure relates to a cold therapy apparatus that employs a removable coolant heat exchange unit, which can be placed in a cold environment for a period of time to remove heat from its coolant to reduce its temperature, and which can be re-coupled with the cold therapy apparatus to serve as its thermal reserve during cold therapy.

BACKGROUND OF THE INVENTION

The benefits of cold therapy in treatment of various human and animal conditions are well documented. Various apparatuses have been devised to achieve the desired transfer of heat between a creature, human or animal, and such an apparatus. A classic examples is the ice pack. Modern medicine now recommends specific amounts of heat transfer for specific durations of time as are indicated for various physical ailments and conditions. For example, soft tissue injuries often indicate cold therapy immediately after injury for a recommended period of time.

Traditionally, cold therapy has been accomplished with the affected individual in a fixed position. Such thinking corresponded to the concept of limited physical movement of the patient during cold therapy or recovery from injury. However, patients often desire some degree of mobility during therapy. Movement and mobility during cold therapy, generally thermal therapy, is acceptable in the case where there is no undue strain to the affected portion of the patient's body. In fact, some movement of the affected area is tolerable, and sometimes even desirable. Given the need and desire for mobility during thermal therapy, some devices and apparatus have been brought to market. One example is the ice chest and bladder cold therapy system. In the ice chest system, the user carries an insulated chest that contains a mixture of ice and water, along with a pump and battery. A pair of hoses is coupled between the chest and pump, and to a thermal body wrap, which is held against the affected portion of the patient's body. The patient is able to carry the chest as they move about. Such systems are cost effective, but some significant limitations to this approach are the size and bulk of the systems for carrying about, and the cold temperature available with ice water. Thermoelectric cooling systems are also know, which force heat transfer by the Peltier Effect, however such system are not generally cost effective in practice.

In the case of a cold therapy apparatus that relies upon a chilled substance, many of the prior art devices employ a reserve of water and ice, where the water portion is circulated through the thermal body wrap. As is well understood, that water portion of an ice water mixture will be near 32° Fahrenheit, which carries a risk of excessive temperature drop in the affect area of the body being treated. This type of system also requires a substantial bulk, the need to replenish the ice supply, and the requirement to disposed water resulting from the melted ice. Thus it can be appreciated that there is a need in the art for a cold therapy apparatus and method to address the problems in the prior art.

SUMMARY OF THE INVENTION

The need in the art is addressed by the apparatuses and methods of the present invention. The present disclosure teaches a cold therapy apparatus for removing heat from a body, such as a human body. The apparatus includes a thermal body wrap that is coupled through an umbilical tube assembly to a control unit, for circulating a thermal fluid to remove heat from a body with which the thermal body wrap may be engaged. The control unit includes a pump that is fluidly coupled to circulate the thermal fluid from a supply coupler, through the umbilical tube assembly and the thermal body wrap, to a return coupler. A coolant heat exchange assembly includes a coolant tank that is filled with a coolant and has a heat exchanger inside that is immersed in the coolant. The heat exchanger fluidly couples to a thermal fluid inlet coupler and a thermal fluid outlet coupler, both present an exterior surface of the coolant tank, to circulate the thermal fluid through it, and thereby transfer heat from the thermal fluid to the coolant. The supply coupler and the return coupler are removably engaged with the thermal fluid inlet coupler and the thermal fluid outlet coupler, respectively, to enable the thermal fluid to circulate between the heat exchanger and the thermal body wrap, while enabling separation of the coolant heat exchange assembly from the control unit such that the coolant heat exchange assembly may be intermittently located in a cold environment to remove heat from the coolant.

In a specific embodiment, the foregoing apparatus further includes an insulated enclosure with an opening for receiving the coolant heat exchange assembly while it is engaged with the control unit, to thereby substantially insulate the coolant heat exchange assembly against the coupling of external heat thereinto. In a refinement to this embodiment, a portion of the insulated enclosure is fixed to the coolant heat exchange assembly and is configured such that the opening is substantially closed by the portion when the coolant heat exchange assembly is inserted into the insulated enclosure.

In a specific embodiment of the foregoing apparatus, the heat exchanger includes an inlet manifold that is fluidly coupled to an outlet manifold through plural heat exchange tubes, and, the inlet manifold is fluidly coupled to the thermal fluid inlet coupler, and the outlet manifold is fluidly coupled to the thermal fluid outlet coupler.

In a specific embodiment of the foregoing apparatus, the coolant tank includes a first coolant tank portion and a second coolant tank portion, which are located on opposing sides of the heat exchanger, and contain a first portion of the coolant and a second portion of the coolant, respectively, such that the heat exchanger is thermally exposed on opposing sides thereof to both of the first coolant portion and the second coolant portion.

In a specific embodiment of the foregoing apparatus, the thermal fluid inlet coupler and the thermal fluid outlet coupler are coupled through at least one of the first coolant tank portion and the second coolant tank portion.

In specific embodiment of the foregoing apparatus, the first coolant tank portion and the second coolant tank portion are partially enclosed by a first coolant tank cover and a second coolant tank cover, respectively. In a refinement to this embodiment, the thermal fluid inlet coupler and the thermal fluid outlet coupler are coupled through at least one of the first coolant tank cover and the second coolant tank cover.

In a specific embodiment of the foregoing apparatus, the first coolant tank cover and the first coolant tank portion, and second coolant tank cover and the second coolant tank portion, are formed of a thermoplastic material having spring clips and cooperatively aligned lugs, monolithically molded therewith, and disposed therebetween, to facilitate assembly by spring-snap action.

In a specific embodiment of the foregoing apparatus, the heat exchanger includes a first heat exchanger portion and a second heat exchanger portion, which are joined together in clamshell fashion to define plural heat exchange tubes fluidly coupled with an inlet manifold and an outlet manifold. In a refinement to this embodiment, the first heat exchanger portion and the second heat exchanger portion are join together with mechanical fasteners, and have a seal disposed therebetween. In another refinement to this embodiment, the first heat exchanger portion and the second heat exchanger portion are formed of a thermoplastic material having spring clips and cooperatively aligned lugs, monolithically molded therewith, and disposed therebetween, to facilitate assembly by spring-snap action.

In a specific embodiment of the foregoing apparatus, the first coolant tank portion and the first heat exchanger portion are formed together as a unit, and the second coolant tank portion and the second heat exchanger portion are formed together as a unit. In a refinement to this embodiment, the first coolant tank portion and the first heat exchanger portion unit, and the second coolant tank portion and the second heat exchanger portion unit are formed from thermoplastic.

In a specific embodiment of the foregoing apparatus, the first coolant tank portion and the first heat exchanger portion unit, and the second coolant tank portion and the second heat exchanger portion unit are formed of a thermoplastic material having spring clips and cooperatively aligned lugs, monolithically molded therewith, and disposed therebetween, to facilitate assembly by spring-snap action.

In a specific embodiment of the foregoing apparatus, the coolant is water mixed with an additive to prevent freezing above a temperature of minus twenty-fide degrees Fahrenheit, and the thermal fluid is selected from a mixture of water and isopropyl alcohol or propylene glycol, which mixture prevents freezing above a temperature of minus twenty-fide degrees Fahrenheit.

In a specific embodiment of the foregoing apparatus, the supply coupler, the return coupler, the thermal fluid inlet coupler and the thermal fluid outlet coupler are quick-connect tubing couplers with automatic shut-off valves to prevent the thermal fluid from leaking when disconnected.

In a specific embodiment of the foregoing apparatus, the heat exchanger is fabricate from high density polyethylene (HDPE) plastic.

The present disclosure teaches a method for removing heat from a body using a cold therapy apparatus, which includes a control unit with a pump that is fluidly coupled from a supply coupler on the control unit, through an umbilical tube assembly and a thermal body wrap, to a return coupler on the control unit, where the apparatus further includes a coolant heat exchange assembly that has a coolant tank with a heat exchanger inside that is fluidly coupled to a thermal fluid inlet coupler and a thermal fluid outlet coupler, and both disposed on the exterior of the coolant tank. The method includes the steps of filing the coolant tank with a coolant, which immerses the heat exchanger in the coolant, and then placing the coolant heat exchange assembly in a cold environment, to remove heat from the coolant that is in the coolant tank, and then, removing the coolant tank assembly from the cold environment. The method also includes coupling the control unit supply coupler and return coupler with the heat exchange assembly thermal fluid outlet coupler and the thermal fluid inlet coupler, respectively, and, filling the heat exchanger, pump, umbilical tube assembly, and thermal body wrap with a thermal fluid. And, engaging the thermal body wrap with a body from which heat is to be removed, and operating the pump, thereby circulating the thermal fluid between the thermal body wrap and the heat exchanger, passing through the pump, the umbilical tube assembly, the supply coupler, the return coupler, the thermal fluid inlet coupler and the thermal fluid outlet coupler, and thereby enabling the thermal fluid to transfer heat from the body to the coolant.

In a specific embodiment, the foregoing method further includes placing the the coolant heat exchange assembly into an insulated enclosure, which has an opening for receiving the coolant heat exchange assembly, while engaged with the control unit, thereby substantially insulating the coolant heat exchange assembly against the coupling of external heat thereinto.

In a specific embodiment of the foregoing method, the heat exchanger includes an inlet manifold fluidly coupled to an outlet manifold through plural heat exchange tubes, and the inlet manifold is fluidly coupled to the thermal fluid inlet coupler, and the outlet manifold is fluidly coupled to the thermal fluid outlet coupler.

In a specific embodiment of the foregoing method, the coolant tank includes a first coolant tank portion and a second coolant tank portion, which are located on opposing sides of the heat exchanger, and contain a first portion of the coolant and a second portion of the coolant, respectively, thereby thermally exposing the heat exchanger on opposing sides thereof to both of the first coolant portion and the second coolant portion.

In a specific embodiment of the foregoing method, the heat exchanger includes a first heat exchanger portion and a second heat exchanger portion, which are joined together in clamshell fashion to define plural heat exchange tubes fluidly coupled with an inlet manifold and an outlet manifold.

In a specific embodiment of the foregoing method, the first coolant tank portion and the first heat exchanger portion are formed together as a unit, and the second coolant tank portion and the second heat exchanger portion are formed together as a unit.

In a specific embodiment of the foregoing method, the first coolant tank portion and the first heat exchanger portion unit, and the second coolant tank portion and the second heat exchanger portion unit are formed from thermoplastic.

In a specific embodiment of the foregoing method, the coolant is water mixed with a additive to prevent freezing above a temperature of minus twenty-fide degrees Fahrenheit, and, the thermal fluid is selected from a mixture of water and isopropyl alcohol or propylene glycol, which mixture prevents freezing above a temperature of minus twenty-fide degrees Fahrenheit.

In a specific embodiment of the foregoing method, the supply coupler, the return coupler, the thermal fluid inlet coupler and the thermal fluid outlet coupler are quick-connect tubing couplers having automatic shut-off valves therein to prevent the thermal fluid from leaking when disconnected.

BRIEF DESCRIPTION OF THE DRAWINGS

FIG. 1 is a cold therapy apparatus application drawing according to an illustrative embodiment of the present invention.

FIGS. 2a and 2b are drawing of a cold therapy apparatus drawings according to an illustrative embodiment of the present invention.

FIGS. 17a, 17b, and 17c are front view, side section view, and end view drawings, respectively, of a coolant tank and heat exchange molding according to an illustrative embodiment of the present invention.

FIGS. 18a and 18b are isometric view drawings of an insulated enclosure according to an illustrative embodiment of the present invention.

DESCRIPTION OF THE INVENTION

Figure 3:
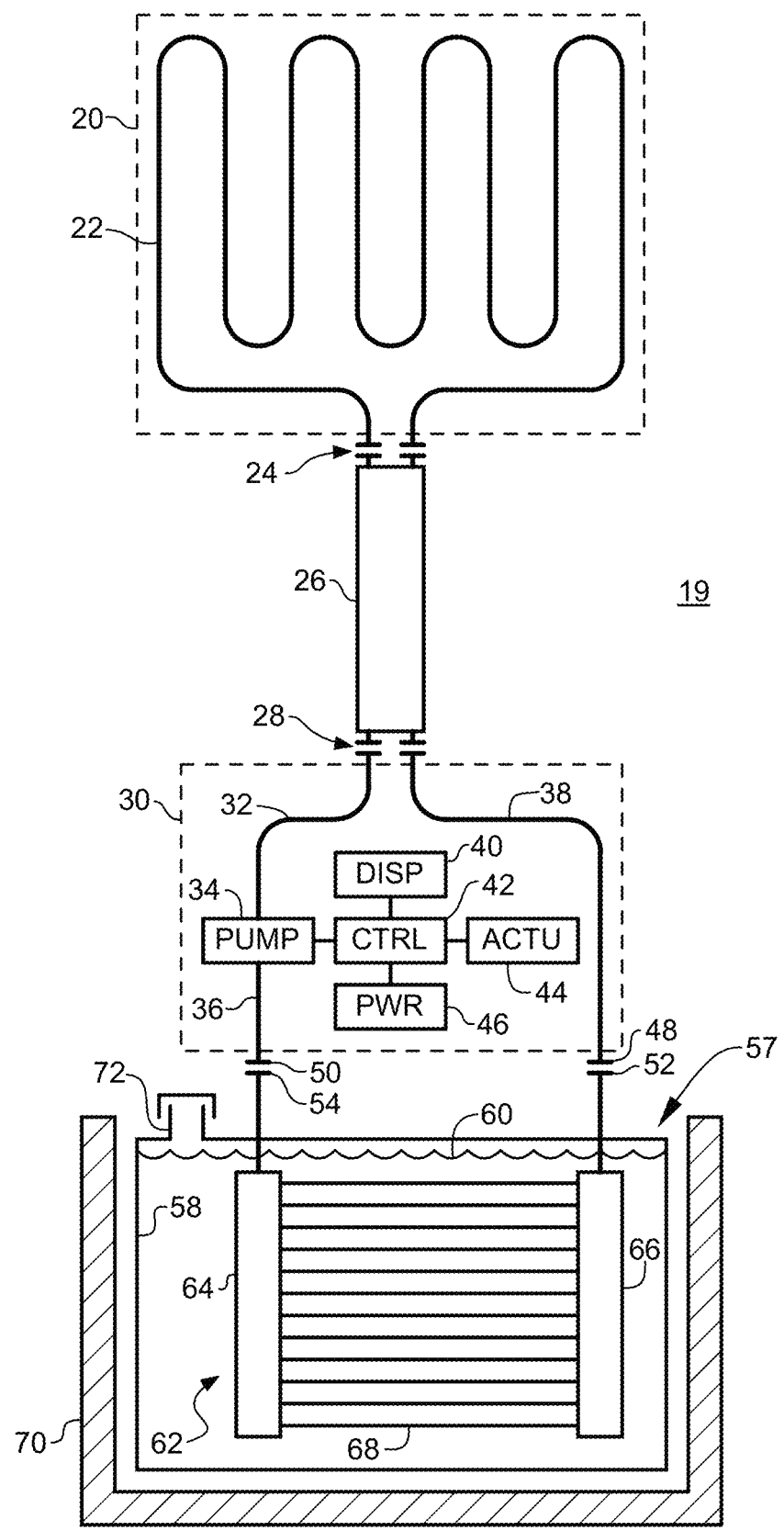
FIG. 3 is a functional block diagram of a cold therapy apparatus according to an illustrative embodiment of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof, and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components, and method steps, have been represented where appropriate by conventional symbols in the drawings, showing only those specific details that are pertinent to understanding the present teachings so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

Under the cold therapy teachings of the present disclosure, a thermal reserve is provided in the form of a coolant that is contained in a coolant tank, and, that coolant tank has a heat exchanger located inside, which is immersed in the coolant. A thermal fluid is circulated through the heat exchanger, to transfer heat from the thermal fluid and into the coolant. As such, the temperature of the thermal fluid is reduced as it passes through the heat exchanger, and is then pumped to a thermal body wrap, where heat from the body is transferred to the thermal fluid, increasing its temperature, and which is then returned to the heat exchanger. Thus, the thermal reserve, the coolant, is a separate substance from the thermal fluid, which is pumped through a thermal fluid circuit that includes the thermal body wrap. A virtue of this arrangement is that the coolant and the thermal fluid can be different materials with different thermodynamic characteristics. Another virtue of this design is that the coolant and coolant tank can be removed from the overall apparatus, chilled, and reused, without the need or mess associated with disposing of, or replacing, the working fluids.

Reference is directed to FIG. 1, which is a cold therapy apparatus 2 application drawing according to an illustrative embodiment of the present invention. An individual 4 with a knee injury has a thermal body wrap 6 fastened thereabout. The thermal body wrap 6 is fluidly coupled by an umbilical tube assembly 8 to a cold therapy apparatus 10. The cold therapy apparatus 10 is of compact proportions and is suitable for portable operation, including carrying in the hand of the individual 4.

Reference is directed to FIGS. 2a and 2b, which are drawing of a cold therapy apparatus according to an illustrative embodiment of the present invention. The cold therapy apparatus 10 includes a user interface 18 with power and operational controls, and a carrying handle 16 formed integrally therewith. The cold therapy apparatus 10 is thermally insulated and receives 14 a coolant heat exchange assembly 12 therein, which is thereby insulated from external heat sources. An umbilical tube assembly 8 couples the coolant heat exchange assembly 12 to a thermal body wrap (not shown). A benefit of this arrangement is that the coolant heat exchange assembly 12, when removed from the apparatus 10, can be placed in a freezer, or other cold environment, to remove heat therefrom, to thereby "recharge" the unit for continued operation. And, the user may be provided with more than one coolant heat exchange assembly 12 so that their use may be rotated in sequence, to provide continued thermal therapy.

Reference is directed to FIG. 3, which is a functional block diagram of a cold therapy apparatus 19 according to an illustrative embodiment of the present invention. A thermal body wrap 20 is coupled through an umbilical tube assembly 26 to a control unit 30, which is, in turn, coupled to a coolant heat exchange assembly 57, which is located within an insulated enclosure 70. The thermal body wrap 20 may take several forms, as are known to those skilled in the art. These may be shaped to fit particular body parts, or may employ a generic configuration. Within the thermal body wrap 20 is a circuitous fluid path 22, through which a working thermal transfer fluid is circulated. Hereinafter referred to a "thermal fluid." The umbilical tube assembly 26 comprises a pair of flexible tubes within an insulated sheath, and is coupled to the thermal body wrap by a first pair of couplers 24, or by permanent connection. The thermal fluid is circulated through the umbilical tube assembly 26 to and from the thermal body wrap 20.

The control unit 30 in FIG. 3 is coupled to the umbilical tube assembly 26 by a second pair of couplers 28, or by permanent connection. The couplers 24, 28 may be selected from a variety of tubing couplers known to those skilled in the art, and quick-couplers are a good choice for convenience. Couplers 24, 28 with built-in shut off valves are useful in preventing thermal fluid leakage when disconnected. Within the control unit are located plural fluid and electrical circuits, which are presented in function block diagram form in FIG. 3. A pump 34 is coupled between tubes 32, 36, which serves as the motive force for circulating the thermal fluid in the cold therapy apparatus 19. Tube 32 is coupled 28 to the umbilical tube assembly 26, and tube 36 is terminated at a thermal fluid inlet coupler 50. The pump 24 may be any of the type known to those skilled in the art, with centrifugal and diaphragm pumps suitable for 12 Vdc nominal operation being good options. The other half of the fluid circuit is tube 38 which couples coupler 28 to the umbilical tube assembly 26 and a thermal fluid outlet coupler 48 on the control unit 30. The tubes 32, 36, 38 may be rigid or flexible, fabricated from metals or polymers. In the illustrative embodiment, flexible 3/16" diameter polymeric tubing suitable for use with the thermal fluid is employed. The thermal fluid in the illustrative embodiment is a mixture of water and isopropyl alcohol the prevents freezing at temperatures above −25° F. Other additives and fluids may be utilized.

The electrical circuit functions in FIG. 3 include the aforementioned pump 34, which is connected to a control circuit 42 for providing power thereto at selected times and for selected periods of time. A typical run time is for thirty minutes, however this may be adjusted to suit therapeutic requirements. An actuator 44 is connected to the control circuit 42 for initiating, adjusting, and terminating operation of the pump 34 and other circuit functions. A simple on/off switch may be employed, or a more advanced timing circuit, or microprocessor controlled circuit, depending on the sophistication of system control that may be desired. A power source 46, or power supply interface, is employed for providing electrical power to pump 34 and related circuitry. In the illustrative embodiment, 12 Vdc nominal power is employed, either by battery source or mains powered transformer operation. In addition, a user interface display 40 may be provided to indicate status of operation of the cold therapy apparatus 19. In the illustrative embodiment, a pump-on indicator light is provided, and a count-down timer by sequential illumination of LEDs is employed. A digital display may also be provided.

The thermal fluid supply coupler 50 and return coupler 52 of the control assembly 30 are selectively engaged with corresponding thermal fluid outlet coupler 54 and thermal fluid inlet coupler 52, respectively, in a coolant heat exchange assembly 57. Quick couplers with internal shut-off valves are a suitable choice, but other couplers known to those skilled in the art may also be employed. The coolant heat exchange assembly 57 includes a coolant tank 58, which is filled with a liquid coolant 60 through a coolant fill port 72. The coolant 60 in the illustrative embodiment is a water-based mixture that prevents freezing at temperatures above −25° F., which includes water and a suitable additive. Another illustrative embodiment provides an instant cold pack system that consists of a suitable amount of ammonium nitrate, calcium ammonium nitrate or urea inside that coolant tank, to which water is added to fill the tank. When this occurs, the material dissolves and an endothermic reaction occurs, which quickly absorbs heat from the surroundings, and quickly lowers the coolant temperature. In another embodiment, the apparatus is provided to the end user with the coolant 60 additive and water mixture already filled into the coolant tank 58. Within the coolant tank 58 is heat exchanger 62, immersed in the coolant 60, and coupled to the thermal fluid outlet coupler 54 and thermal fluid inlet coupler 52 such that thermal fluid is circulated through the heat exchanger 62 to transfer heat into the coolant 60.

In the illustrative embodiment of FIG. 3, the heat exchange assembly 62 consists of an inlet manifold 66 coupled though plural heat exchange tubes 68 to and outlet manifold 64. The inlet manifold 66 is fluidly coupled to the thermal fluid inlet coupler 52, and the outlet manifold 64 is fluidly coupled to thermal fluid outlet coupler 54, thereby completing the fluid circuit through the heat exchange assembly 62. In the illustrative embodiment, the coolant heat exchange assembly 57 of the thermal cooling apparatus 19 is positioned within an insulated enclosure 70 while engaged with the cold therapy apparatus 19 to reduce unwanted heat transfer into the coolant, thereby extending available thermal reserve for therapy purposes.

Figure 4:
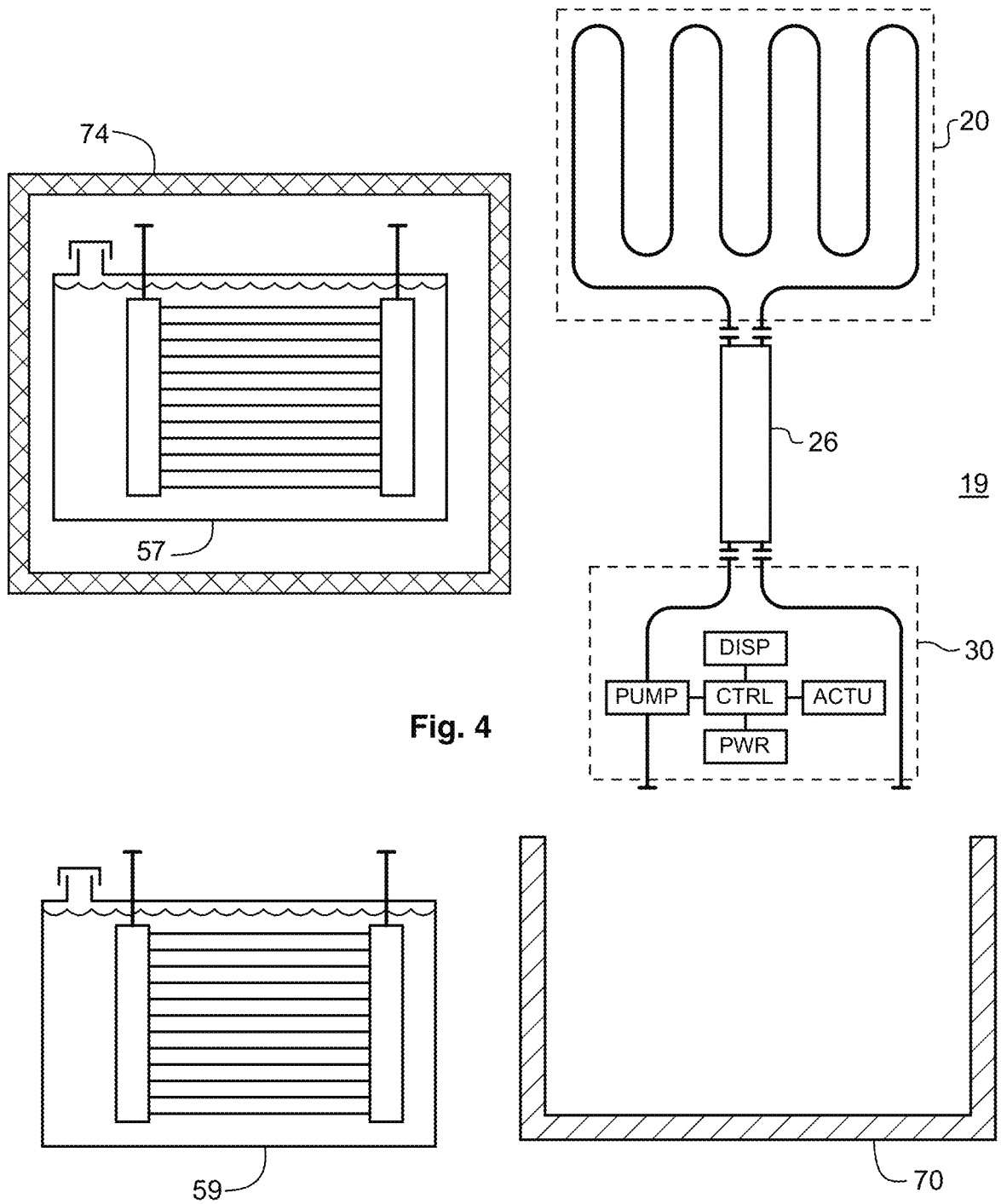
FIG. 4 is a functional block diagram of a cold therapy system according to an illustrative embodiment of the present invention.
Figure 5:
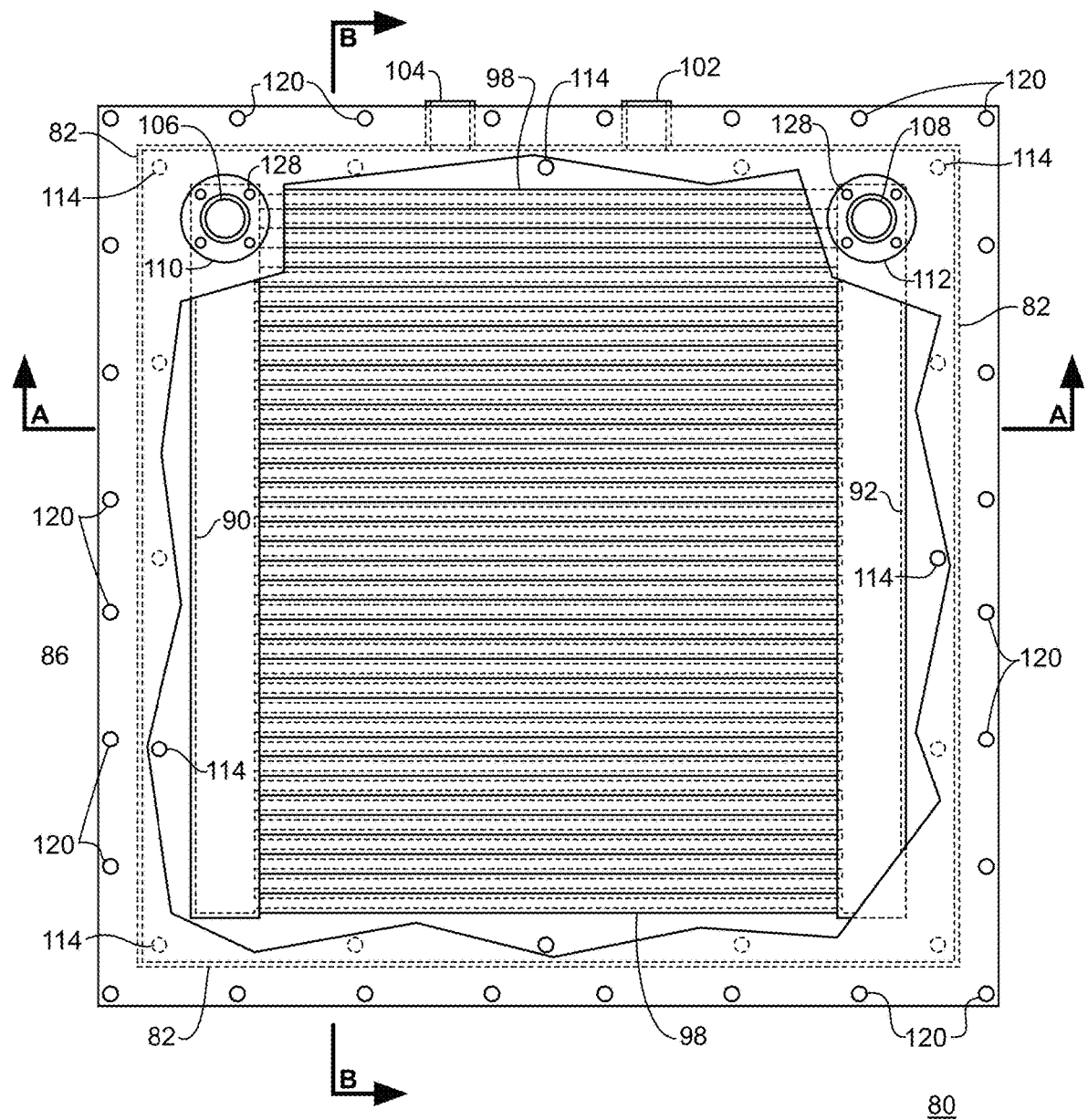
FIG. 5 is a front view drawing of a coolant tank and heat exchange assembly according to an illustrative embodiment of the present invention.
Figure 6:
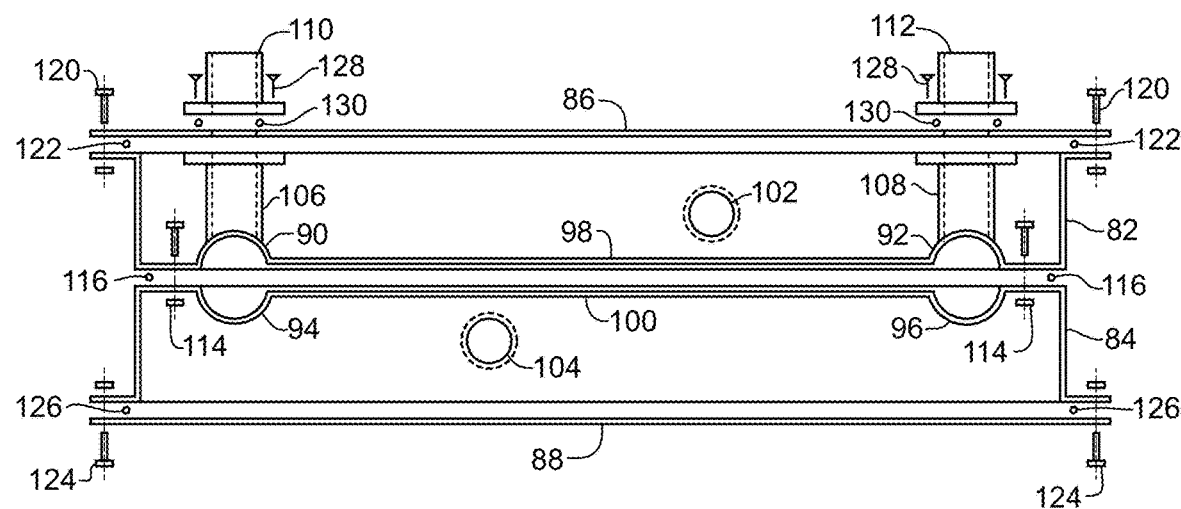
FIG. 6 is an exploded section view drawing of a coolant tank and heat exchange assembly according to an illustrative embodiment of the present invention.
Figure 7:
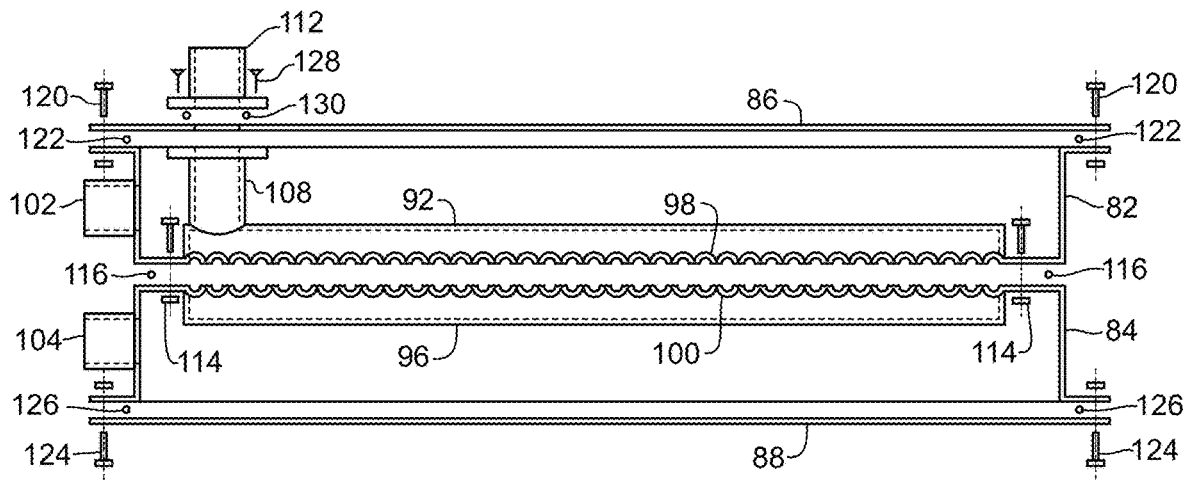
FIG. 7 is an exploded section view drawing of a coolant tank and heat exchange assembly according to an illustrative embodiment of the present invention.

Reference is directed to FIG. 4, which is a functional block diagram of a cold therapy system according to an illustrative embodiment of the present invention. FIG. 4 corresponds with FIG. 3. In FIG. 4, the cold therapy apparatus 19 is presented, but with the coolant heat exchange assembly 57 removed from the insulated enclosure 70, and placed into a freezer 74, or other cold environment. After a period of time, the coolant 60 temperature will stabilize at the freezer 74 temperature and be ready for reconnection to the cold therapy apparatus 19. Note that the user of such an apparatus may be provided with two or more coolant heat exchange assemblies 57, 59, such that they can be rotated in service between cold therapy use and a freezer to 'recharge' for subsequent use.

Reference is directed to FIGS. 5, 6, 7, 8, and 9, which are a front view drawing, exploded section view drawings, and section view drawings, as indicated, of a coolant heat exchange assembly 80 according to an illustrative embodiment of the present invention. One aspect of the apparatus and methods of the present disclosure is the requirement to provide a cost effective cold therapy apparatus in view of prior art designs, but that also provides improved performance. The design of the coolant heat exchange assembly 80 represents one opportunity to achieve these objectives. The coolant heat exchange assembly 80 is low cost because it is molded of a few thermoplastic moldings that are conveniently sealed and joint together in a manner not formerly utilized in such devices. In the illustrative embodiment, that thermoplastic is high density polyethylene (HDPE). HDPE has good molding characteristics, low cost, and has exhibited useful thermal transfer properties between the coolant and thermal fluid within the heat exchanger portion of the coolant heat exchange assembly 80. Other thermoplastics can be employed, including acrylonitrile butadiene styrene (ABS), polycarbonate, polyether sulfone, polyethylene, polypropylene, polyvinyl chloride, polyvinylidene fluoride, and others.

Figure 8:
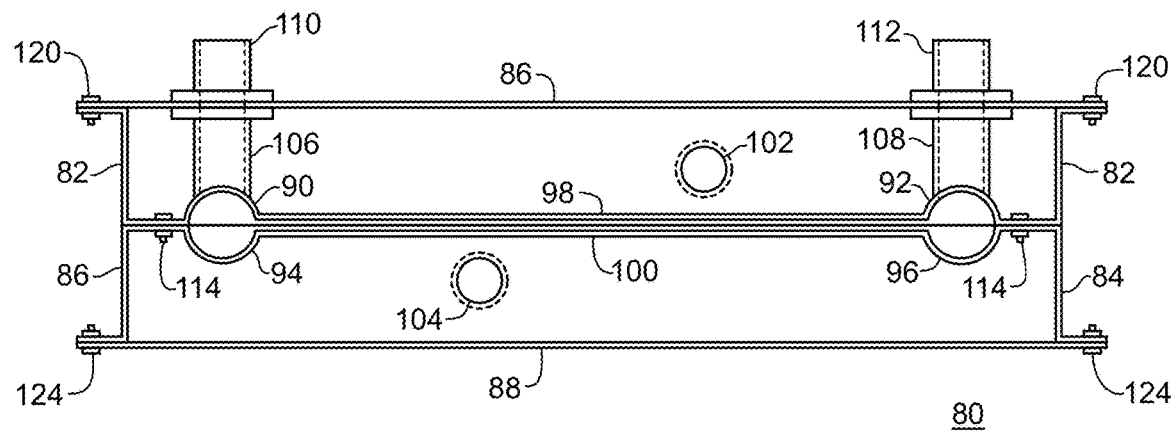
FIG. 8 is a section view drawing of a coolant tank and heat exchange assembly according to an illustrative embodiment of the present invention.
Figure 9:
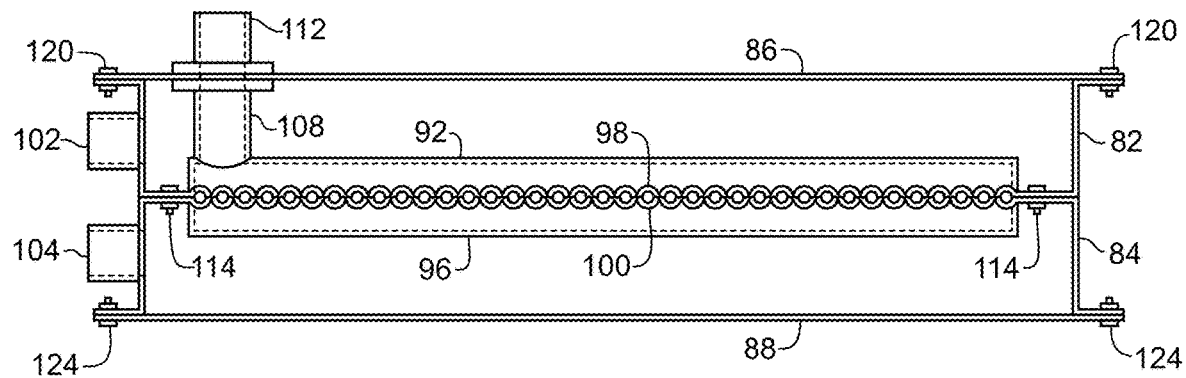
FIG. 9 is a section view drawing of a coolant tank and heat exchange assembly according to an illustrative embodiment of the present invention.

The heat exchanger and the coolant tank are formed together by assembling the several moldings illustrated in FIGS. 5 through 9. The heat exchanger is formed by joining two moldings 82, 84, which are formed to define opposing halves of plural heat exchange tubes 98, 100, and opposing halves of the outlet manifold 90, 94, and the inlet manifold 92, 96, which fluidly coupled with the plural heat exchange tubes 98, 100, as illustrated. An O-ring seal 116 is disposed between these two moldings 82, 84, and then the moldings 82, 84 are joined in clamshell fashion with plural mechanical fastener sets 114 to define the completed heat exchanger as illustrated in FIGS. 8-9. The fasteners can be any suitable fastener, and in this illustrative embodiment screw and nut sets 114 are utilized. Alternatively, screws that engage polymeric bosses in the opposing side of the molding can cut threads therein and secure them together. The outlet manifold 90, 94 is coupled to an outlet conduit 106, and the inlet manifold 92,96 is coupled to inlet conduit 108, and these are molding with molding 82. Note that the perimeter of the moldings 82, 86 include sidewalls with flanges, as illustrated, to define a volumetric space which serves as a first and second coolant tank portion. The coolant tank portions are then fully enclosed by coolant tank covers 86, 88.

In FIGS. 5 through 9, the two coolant tank portions are defined by moldings 82, 84 and covers 86, 88. Each portion includes a coolant fill port 102, 104 through the side walls of moldings 82, 84, which provide a means for filling with coolant. The covers 86, 88 are joined with moldings 82, 84 using plural mechanical fasteners 120, which are the same as the mechanical fasteners 114, in that screw and nut sets, or screw and boss connections can be employed. The covers 86 and 88 are also sealed using O-rings 122, 126, respectively, about their perimeters, as illustrated. The inlet and outlet conduits 106, 108 align with outlet couplers 110, 112, respectively, through holes in cover 86. These conduits and couplers are joined with flanges sealed with O-rings 130, and mechanical fasteners 128, as illustrated. With this assembled arrangement, the heat exchanger is fluidly coupled from the inlet coupler 112, through the inlet manifold 92, 96, through the plural heat exchange tunes 98, 100, through the outlet manifold 90, 94, and out the outlet coupler 110. And the two portions of the coolant tanks are defined by the moldings 82, 84 and covers 86, 88, as illustrated. The heat exchanger is fully immersed in the coolant during operation, with a first portion on one side and a second portion on the other side.

Figure 10C:
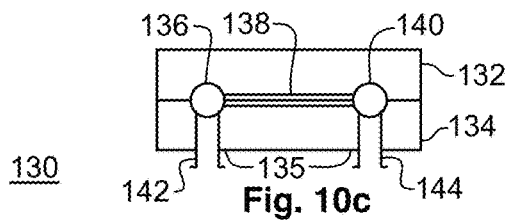
FIGS. 10a, 10b, and 10c are front, side, and end section view drawings of a coolant tank and heat exchange assembly according to an illustrative embodiment of the present invention.
Figure 10B:
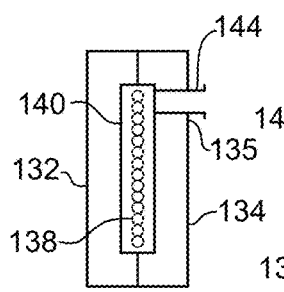
Figure 10A:
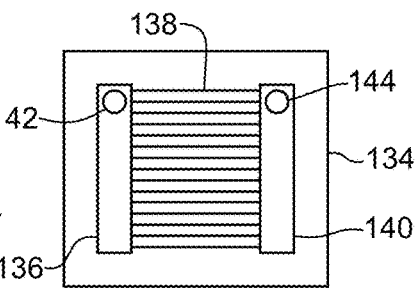

Reference is directed to FIGS. 10a, 10b, and 10c, which are front, side, and end section view drawings of a coolant heat exchange assembly 130 according to an illustrative embodiment of the present invention. These drawings illustrate one orientation of the inlet conduit 144 and outlet conduit 142 through the cover area 135 of the assembly 130. Note the orientation of the heat exchange tubes 138, the inlet manifold 140, the outlet manifold 136, and the two coolant tank portions 132, 134.

Figure 11C:
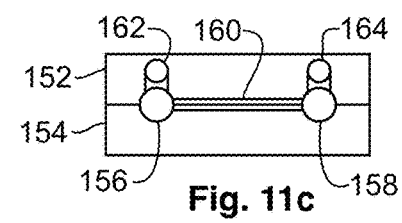
FIGS. 11a, 11b, and 11c are front, side, and end section view drawings of a coolant tank and heat exchange assembly according to an illustrative embodiment of the present invention.
Figure 11B:
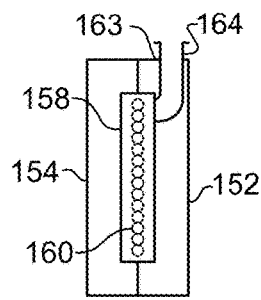
Figure 11A:
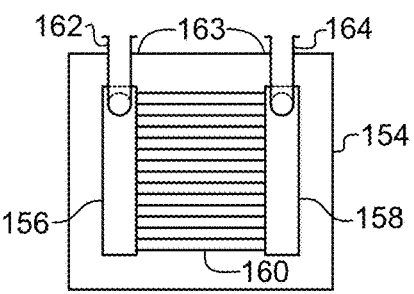

Reference is directed to FIGS. 11a, 11b, and 11c, which are front, side, and end section view drawings of a coolant heat exchange assembly 150 according to an illustrative embodiment of the present invention. These drawings illustrate another orientation of the inlet conduit 164 and outlet conduit 162 through an end wall portion 163 of the assembly 150. Note the orientation of the heat exchange tubes 160, the inlet manifold 158, the outlet manifold 156, and the two coolant tank portions 152, 154.

Figure 12C:
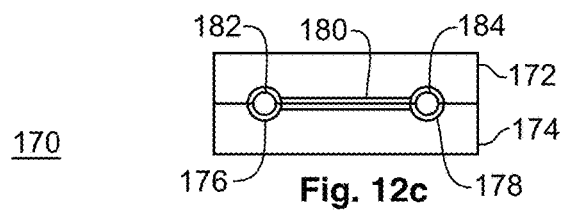
FIGS. 12a, 12b, and 12c are front, side, and end section view drawings of a coolant tank and heat exchange assembly according to an illustrative embodiment of the present invention.
Figure 12B:
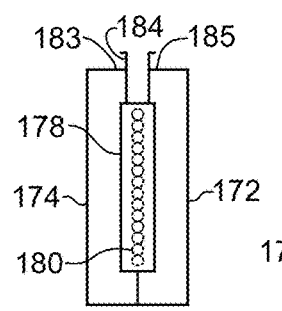
Figure 12A:
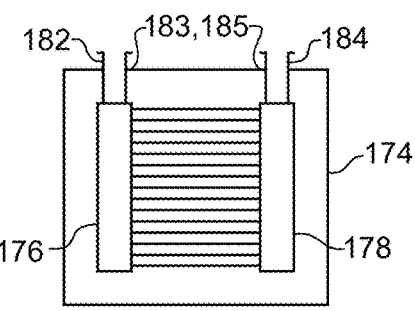

Reference is directed to FIGS. 12a, 12b, and 12c, which are front, side, and end section view drawings of a coolant heat exchange assembly 170 according to an illustrative embodiment of the present invention. These drawings illustrate another orientation of the inlet conduit 184 and outlet conduit 182 through two end wall portions 183, 185 of the two coolant tank portions 172, 174 of the assembly 170. Note the orientation of the heat exchange tubes 180, the inlet manifold 178, the outlet manifold 176, and the two coolant tank portions 172, 174.

Figure 13A:
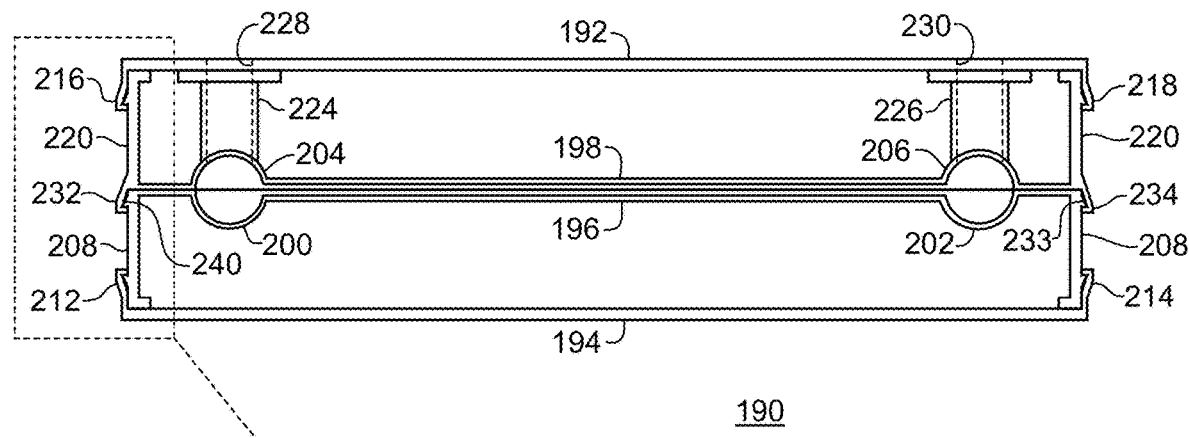
FIGS. 13a and 13b are a section view drawing and a detailed section view drawing, respectively, of a coolant tank and heat exchange assembly according to an illustrative embodiment of the present invention.
Figure 13B:
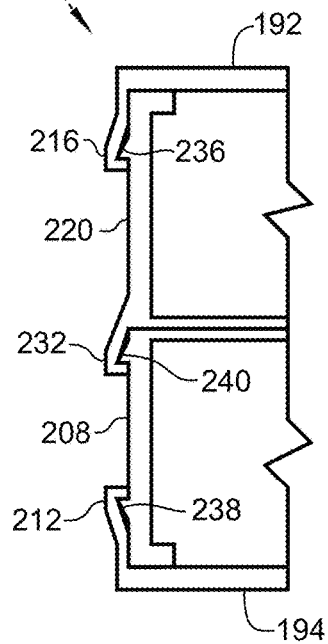

Reference is directed to FIGS. 13a and 13b, which are a section view drawing and a detailed section view drawing, respectively, of a heat exchanger assembly 190 according to an illustrative embodiment of the present invention. In the prior embodiments, mechanical fasteners were employed to join the various moldings together. In this embodiment, spring clips and cooperatively aligned lugs, which are molded together with the various moldings, are employed, thereby eliminating the need and costs associated with separate mechanical fasteners. In FIG. 13a, an upper molding 220 and a lower molding 208 are joined together. These moldings define the plural heat exchange tubes 196, 198, the inlet manifold 206, 202, the outlet manifold 204, 200, as well as the inlet conduit 226 and outlet conduit 224, in similar fashion as the previously discussed illustrative embodiments. On the right side of moldings 220, 208 is a spring clip 234 and cooperatively aligned lug 233. On the left side of these moldings is a spring clip 232 and cooperatively aligned lug 240. As the two moldings 220, 208 are joined together, the spring clips 234, 232 ride over their respective lugs 233, 240 and snap together. The spring action results from the elastic characteristic of the thermoplastic from which the moldings 220, 208 are formed.

In FIG. 13a, the upper cover 192 has spring clips 216, 218 illustrated on its left and right side, and, the lower cover 194 has spring clips 212, 214 illustrated on its left and right sides. There are spring clips located all about the periphery of these covers 192, 194 (not shown). The upper cover 192 also has holes formed therethrough 228, 230, aligned with the inlet conduit 226 and outlet conduit 224. FIG. 13b illustrates the cooperative arrangement of the spring clips and lugs. In particular, the upper molding 220 has spring clip 232, which aligns with cooperative lug 240 on the lower molding 208. The upper cover 192 has spring clip 216, which aligns with cooperative lug 236 on the upper molding 220. Similarly, the lower cover 194 has spring clip 212, which aligns with cooperative lug 238 on the lower molding 208. With this arrangement, the entire coolant heat exchange assembly 190 can be 'snapped' together without the use of separate mechanical fasteners. Also note that seals (not shown), such as O-ring seals, as disposed between the several moldings to prevent leakage of the coolant and thermal fluid.

Figure 14C:
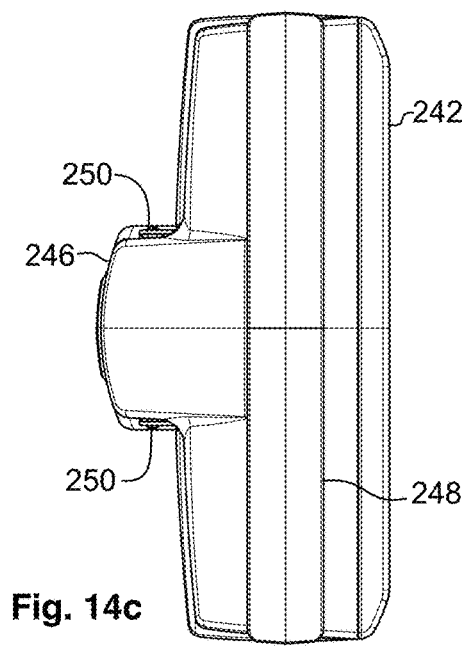
FIGS. 14a, 14b, and 14c are front view, side view, and end view drawings, respectively, of a cold therapy apparatus according to an illustrative embodiment of the present invention.
Figure 14A:
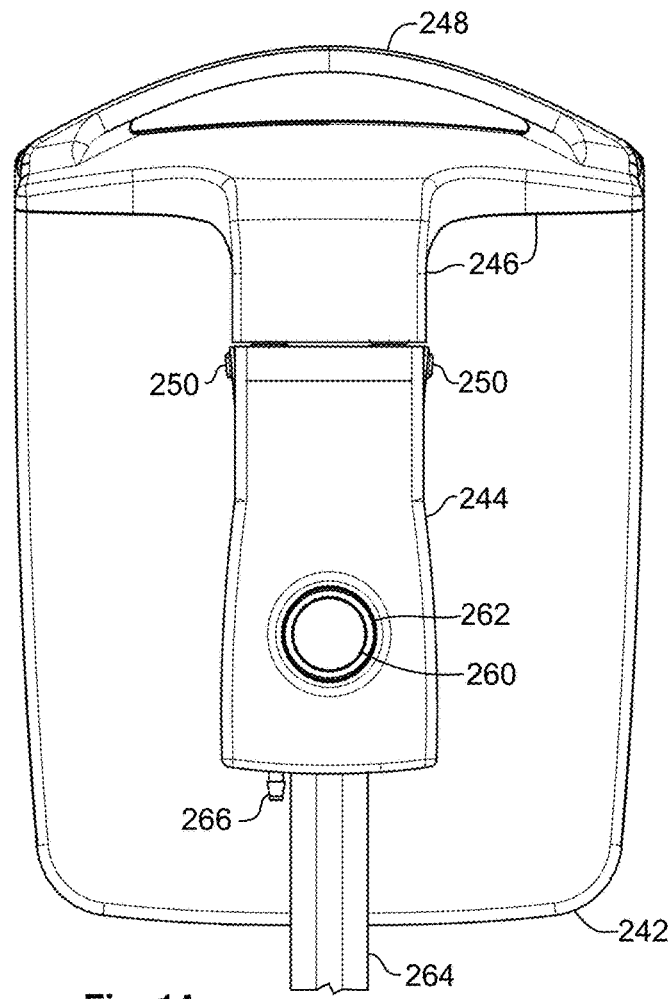
Figure 14B:
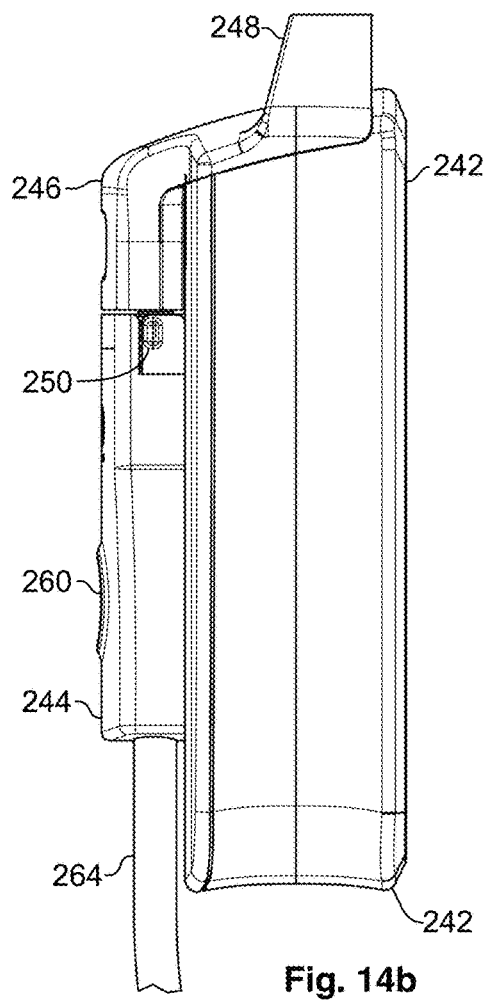

Reference is directed to FIGS. 14a, 14b, and 14c, which are front view, side view, and end view drawings, respectively, of a cold therapy apparatus 247 according to an illustrative embodiment of the present invention. These exterior views illustrate the insulated enclosure 242 with an upper insulated portion 246, which encloses a coolant heat exchange assembly (not shown) therein. The upper portion 246 includes a carry handle 248 for user convenience. A control unit 244 engages the upper insulated portion 246, which conceals a pair of thermal fluid couplers (not shown), and is selectively releasable with spring releases 250. The control unit 244 includes an actuator 260 for engaging operation of a pump (not shown) therein, as well as a timer function for controlling the duration of cold therapy. A ring of LED lights 262 encircle the actuator 260, and sequentially illuminate to indicate the during of therapy. In one embodiment, there are four LEDs in the circle, each indicating seven and one-half minutes of a thirty minute therapy session. A hose fitting 266 is presented on the control unit 244 for filling the coolant heat exchange assembly (not shown) and the umbilical tubing assembly 264, with thermal fluid. In other embodiments, hose couplers (not shown) are separated to provide access to fill with thermal fluid. In either configuration, a pump (not shown) in the control unit 244 provides the motive force for circulating thermal fluid into, and air out of, the thermal fluid tubing circuit.

Figure 15:
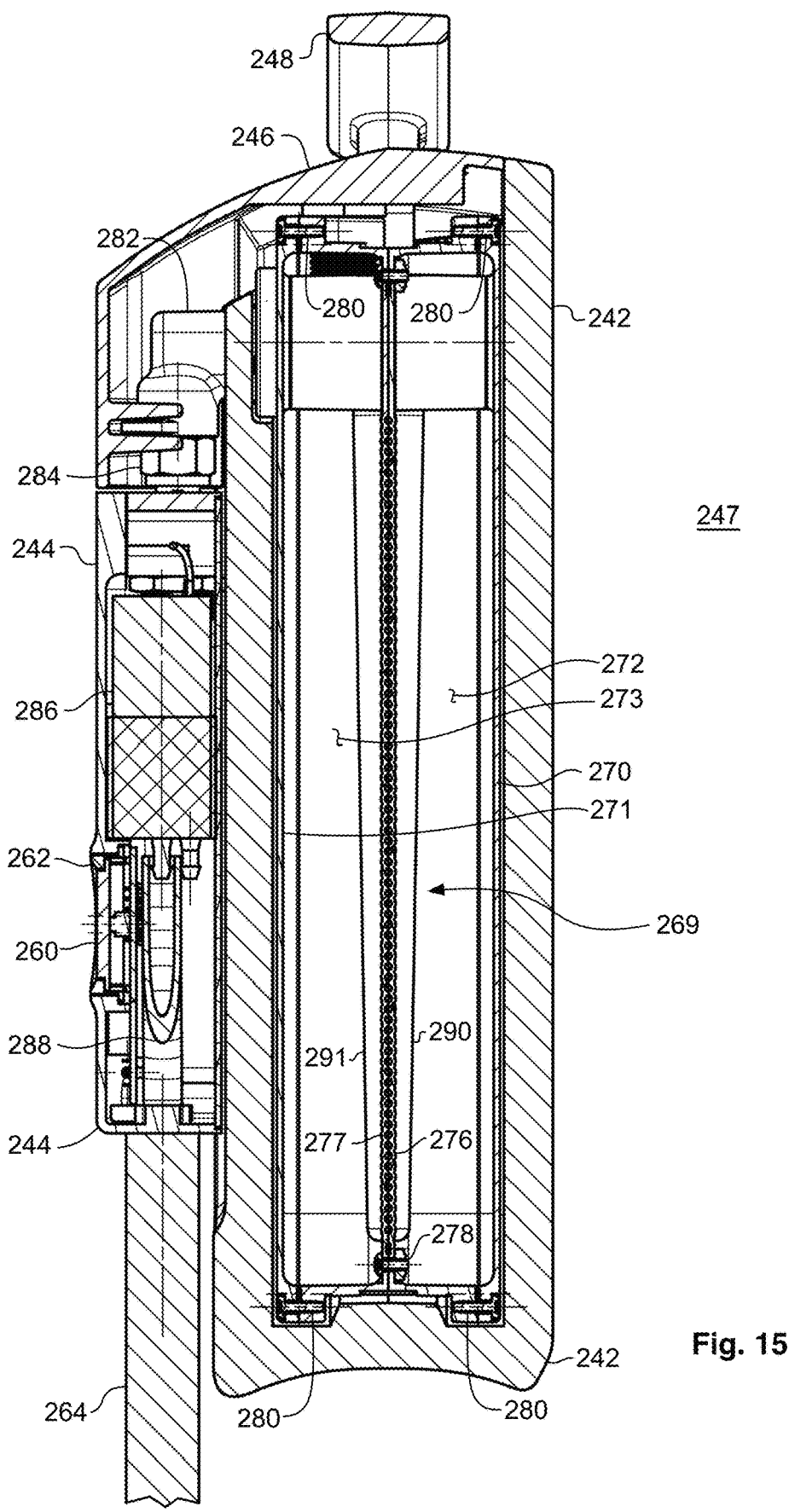
FIG. 15 is a section view drawing of a cold therapy apparatus according to an illustrative embodiment of the present invention.

Reference is directed to FIG. 15, which is a section view drawing of a cold therapy apparatus 247 according to an illustrative embodiment of the present invention. The insulated enclosure 242 and insulated upper portion 246, with carry handle 248, enclose the coolant heat exchange assembly 269. The heat exchanger is located within the coolant heat exchange assembly 269, and is assembled in clamshell fashion, with two halves. In particular, the plural heat exchange tubes 276, 277 are fluidly coupled to a thermal fluid manifold 290, 291, which is fluidly coupled to an elbow fitting 282. Of course, there are both inlet and outlet manifolds and fittings, but only one side is visible in this section view. A thermal fluid coupler 284 is connected to the elbow fitting 282, and serves as a point of connection for the control unit 244. The coolant heat exchange unit 269 is formed to two halves 272, 273 and covers 270, 271 to define two coolant tank portions. The halves 272, 273 are joined with plural mechanical fasteners 278 about their peripheries, and, the covers 270, 271 are joined with the halves 272, 273 with plural mechanical fasteners 280 about their peripheries.

The control unit 244 in FIG. 15 includes a pump 286, which is a diaphragm pump in the illustrative embodiment. The control actuator 260 with LED ring light 262, are presented on the exterior of the control unit 244. Internal tubing 288 connects the thermal fluid circuit, which couples to the umbilical tube assembly 264.

Figure 16:
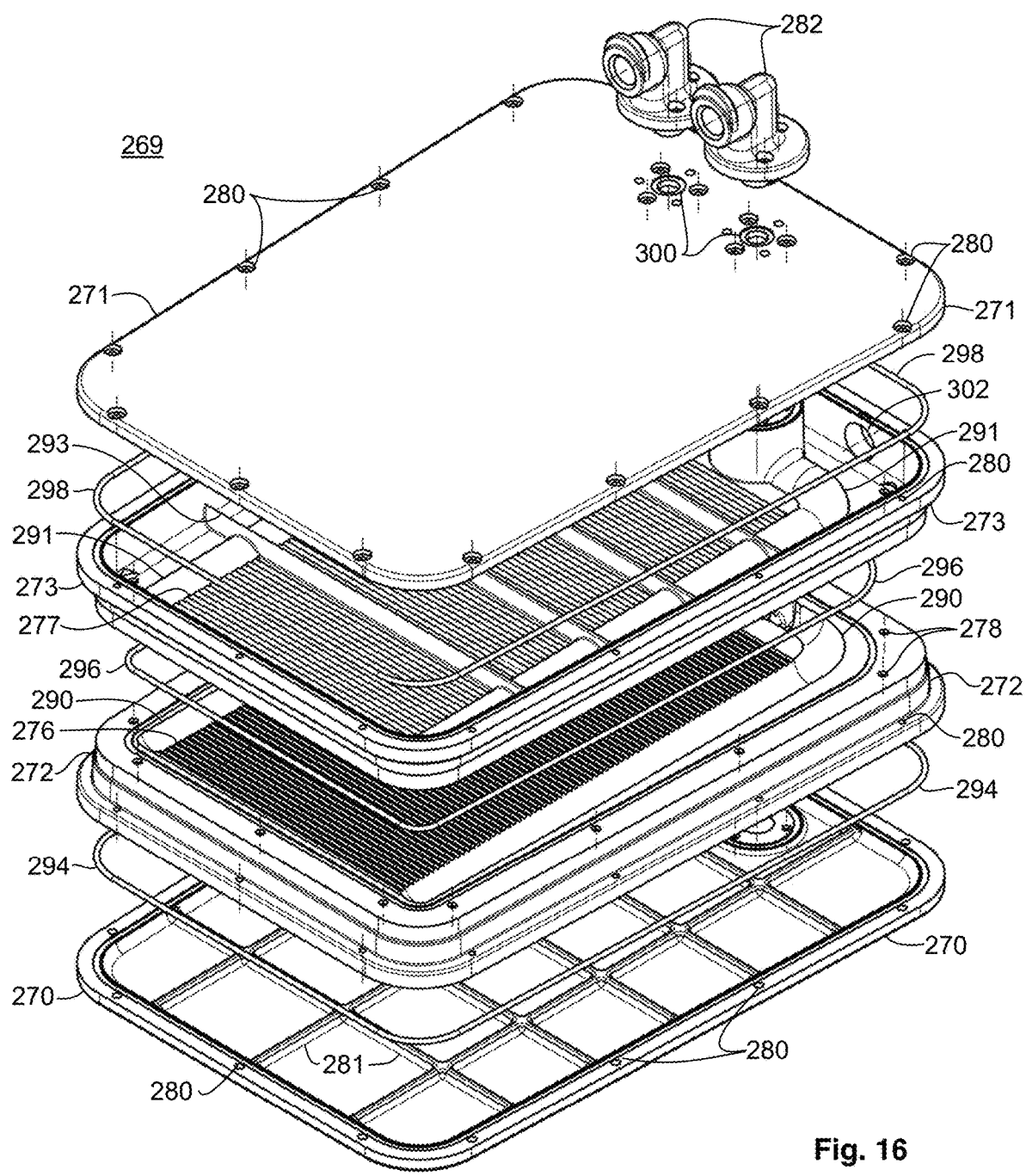
FIG. 16 is an exploded isometric view drawing of a coolant tank and heat exchange assembly according to an illustrative embodiment of the present invention.

Reference is directed to FIG. 16, which is an exploded isometric view drawing of a heat exchanger assembly 269 according to an illustrative embodiment of the present invention. Beginning from the bottom of the drawing sheet, the components of the coolant heat exchange assembly 269 include the lower coolant cover 270 ("lower cover"), the lower O-ring seal 294, the lower coolant tank and heat exchanger molding 272 ("lower molding"), the middle O-ring seal 296, the upper coolant tank and heat exchanger molding 273 ("upper molding"), the upper O-ring seal 298, and the upper coolant tank cover 271 ("upper cover"), as illustrated. The lower cover 270 has plural mechanical fastener holes 280 about it perimeter, and stiffening ribs 281 on its interior surface. The lower O-ring 294 is routed about the perimeter of the lower cover 270. The lower molding 272 also has plural mechanical fastener holes 280 about its perimeter, and a second set of mechanical fastener holes 278 about its perimeter as well. The lower molding 272 includes half of the plural heat exchange tubes 276 and half of the thermal fluid manifolds 290 formed integral with it. The upper molding 273 also has plural mechanical fastener holes 280 about its perimeter. The upper molding 273 includes the other half of the plural heat exchange tubes 277 and the other half of the thermal fluid manifolds 291 formed integral with it. A coolant fill port 302 is proved through upper molding 273 for filling the coolant tank with coolant prior to use. The upper molding 273 also illustrates stiffening ribs 293 to reinforce it against pressure forces. The upper cover 271 has plural mechanical fastener holes 280 form through it, as well as manifold connection and fluid channels 300 formed into it. A pair of fluid elbows 282 are provided for connection to the thermal fluid inlet and outlet couplers (not shown). Note that the covers and moldings are generally symmetrical to one another. For example, both the upper and lower items have stiffening ribs even though they may not be visible in this isometric view. Both of the upper and lower molding also have coolant fill ports 302. The mechanical fastener holes 280 attach the covers to the moldings, and the mechanical fastening holes 278 attach the upper and lower moldings 272, 273 to one another.

Reference is directed to FIGS. 17a, 17b, and 17c, which are front view, side section view, and end view drawings, respectively, of the upper coolant tank and heat exchange molding 271 according to an illustrative embodiment of the present invention. The plural mechanical fastener holes 280 about the perimeter are shown, as well as the second set of mechanical fastening holes 278 just inside of the first set. The thermal fluid manifold 291 can bee seen, with the plural heat exchange members 277 visible as well. The manifolds 291 terminate with a fluid riser 310. Stiffening ribs 306, 308 are provided to reinforce against pressure loads during operation. The coolant fill port 302 is also shown.

Reference is directed to FIGS. 18a and 18b, which are isometric view drawings of an insulated enclosure 242 according to an illustrative embodiment of the present invention. The insulated enclosure 242 serves to insulate the coolant heat exchange unit (not shown) from external sources of heat. Any suitable cellular of fibrous polymeric material may be employed, provided that it as sufficient rigidity to maintain its shape and can engages a cosmetically suitable exterior surface, such as paint. An opening 243 at one end receives the coolant heat exchange unit (not shown). Recesses 245 are provided for passage of the thermal fluid conduits, tubes, or fittings.

Figure 19:
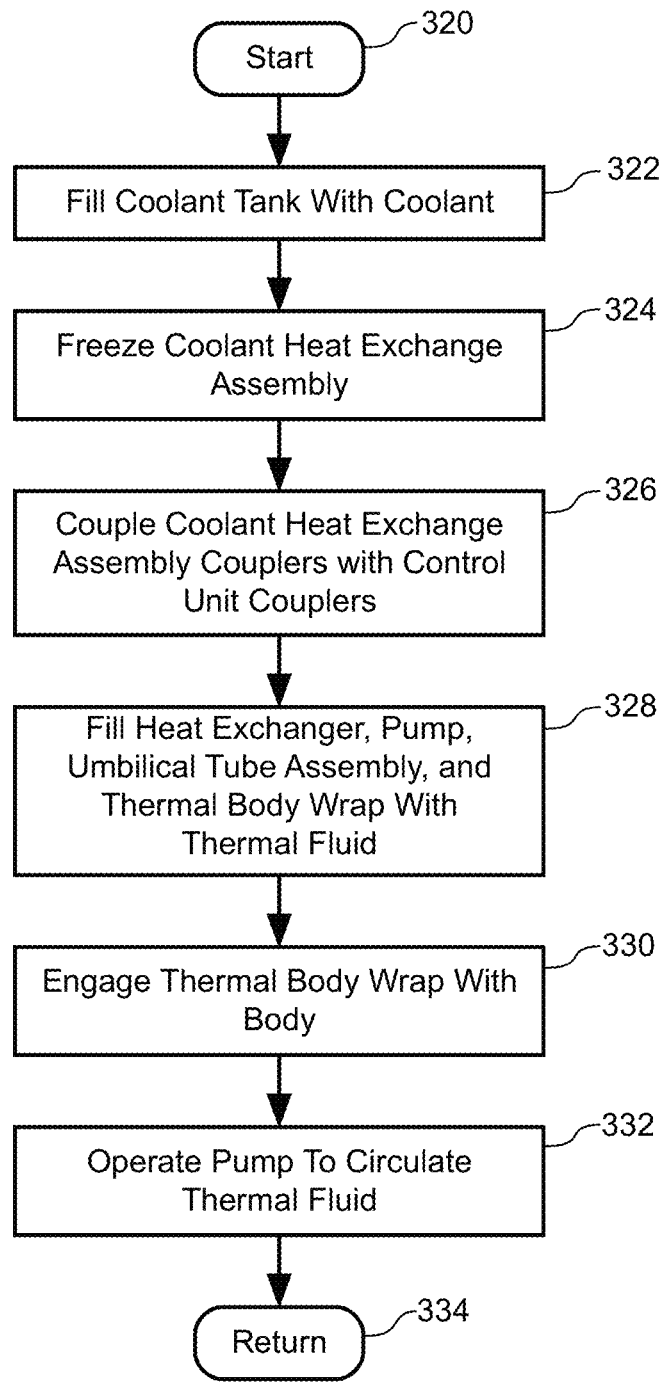
FIG. 19 is a process flow diagram according to an illustrative embodiment of the present invention.

Reference is directed to FIG. 19, which is a process flow diagram showing operation of the subject apparatus by an end user and according to an illustrative embodiment of the present invention. The process starts at step 320 and proceeds to step 322 where the coolant tank is filled through the coolant fill ports with coolant. At step 324, the coolant heat exchange assembly is placed into a freezer for a sufficiently long enough time so that the coolant reaches freezer temperature. At step 326, the coolant heat exchanger is placed into the insulated enclosure and the control unit is coupled to it using the thermal fluid couplers. At step 328, the heat exchanger, pump, umbilical tubing and thermal body wrap are filled with thermal fluid from a separate container using the pump to circulate it. At step 330, the thermal body wrap is engaged with a selection part of the user's body. At step 332, the pump is operated to circulate the thermal fluid, thereby transferring heat from the user's body, into the thermal fluid, and subsequently exchanged into the coolant by the heat exchanger. The process returns at step 334, to be repeated as necessary. In an alternative method, the thermal fluid may be circulated into the coolant and heat exchange unit prior to placing into a freezer such that the volume of thermal fluid that fills the inlet and outlet manifolds and heat exchange tubes is also reduced to freezer temperatures. This approach provides an incremental amount of cooling capacity.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A cold therapy apparatus for removing heat from a body, comprising:
a thermal body wrap coupled through an umbilical tube assembly to a control unit, for circulating a thermal fluid therethrough to thereby remove heat from the body with which said thermal body wrap may be engaged, and wherein
said control unit includes a pump fluidly coupled to circulate said thermal fluid from a supply coupler, through said umbilical tube assembly and said thermal body wrap, to a return coupler;
a coolant heat exchange assembly including a coolant tank filled with a coolant, and having a heat exchanger therein and immersed in said coolant, said heat exchanger fluidly coupled to a thermal fluid inlet coupler and a thermal fluid outlet coupler, both disposed on an exterior surface of said coolant tank, for circulating said thermal fluid therethrough to thereby transfer heat from said thermal fluid to said coolant, and wherein
said heat exchanger includes a first heat exchanger molding portion and a second heat exchanger molding portion, which are cooperatively formed to define opposing halves of plural heat exchange tubes and opposing halves of an inlet manifold and an outlet manifold, which when joined together in clamshell fashion define plural heat exchange tubes, and define an inlet manifold and an outlet manifold that are fluidly coupled to said thermal fluid inlet coupler and said thermal fluid outlet coupler, respectively, and wherein said thermal fluid circulates within and through said plural heat exchange tubes, and wherein
said supply coupler and said return coupler are removably engaged with said thermal fluid inlet coupler and said thermal fluid outlet coupler, respectively, to enable said thermal fluid to circulate between said heat exchanger and said thermal body wrap, while enabling separation of said coolant heat exchange assembly from said control unit such that said coolant heat exchange assembly may be intermittently located in a cold environment to remove heat from said coolant.

2. The apparatus of claim 1, and further comprising:
an insulated enclosure having an opening for receiving said coolant heat exchange assembly while engaged with said control unit, to thereby substantially insulate said coolant heat exchange assembly against the coupling of external heat thereinto.

3. The apparatus of claim 2, and wherein:
a portion of said insulated enclosure is fixed to said coolant heat exchange assembly and proportioned such that said opening is substantially closed by said portion when said coolant heat exchange assembly is inserted into said insulated enclosure.

4. The apparatus of claim 1, and wherein
said coolant tank comprises a first coolant tank portion and a second coolant tank portion, which are located on opposing sides of said heat exchanger, and contain a first portion of said coolant and a second portion of said coolant, respectively, and such that said heat exchanger is thermally exposed on opposing sides thereof to both of said first coolant portion and said second coolant portion.

5. The apparatus of claim 4, and wherein:
said thermal fluid inlet coupler and said thermal fluid outlet coupler are coupled through at least one of said first coolant tank portion and said second coolant tank portion.

6. The apparatus of claim 4, and wherein:
said first coolant tank portion and said second coolant tank portion are partially enclosed by a first coolant tank cover and a second coolant tank cover, respectively.

7. The apparatus of claim 6, and wherein:
said thermal fluid inlet coupler and said thermal fluid outlet coupler are coupled through at least one of said first coolant tank cover and said second coolant tank cover.

8. The apparatus of claim 6, and wherein:
said first coolant tank cover and said first coolant tank portion, and second coolant tank cover and said second coolant tank portion, are formed of a thermoplastic material having spring clips and cooperatively aligned lugs, monolithically molded therewith, and disposed therebetween, to facilitate assembly by spring-snap action.

9. The apparatus of claim 1 and wherein:
said first heat exchanger molding portion and said second heat exchanger molding portion are joined together with mechanical fasteners, and with a seal disposed therebetween.

10. The apparatus of claim 1 and wherein:
said first heat exchanger molding portion and said second heat exchanger molding portion are formed of a thermoplastic material having spring clips and cooperatively aligned lugs, monolithically molded therewith, and disposed therebetween, to facilitate assembly by spring-snap action.

11. The apparatus of claim 1, and wherein:
said first heat exchanger molding portion, and said second heat exchanger molding portion are formed from thermoplastic.

12. The apparatus of claim 11, and wherein:
said first heat exchanger molding portion, and said second heat exchanger molding portion are formed of a thermoplastic material having spring clips and cooperatively aligned lugs, monolithically molded therewith, and disposed therebetween, to facilitate assembly by spring-snap action.

13. The apparatus of claim 1, and wherein:
said coolant is water mixed with an additive to prevent freezing above a temperature of minus twenty-five degrees Fahrenheit, and wherein
said thermal fluid is selected from a mixture of water and isopropyl alcohol or propylene glycol, which mixture prevents freezing above a temperature of minus twenty-five degrees Fahrenheit.

14. The apparatus of claim 1, and wherein:
said supply coupler, said return coupler, said thermal fluid inlet coupler and said thermal fluid outlet coupler are quick-connect tubing couplers having automatic shut-off valves therein to prevent said thermal fluid from leaking when disconnected.

15. The apparatus of claim 1, and wherein:
said heat exchanger is fabricated from high density polyethylene (HDPE) plastic.

16. A method for removing heat from a body using a cold therapy apparatus, which includes a control unit having a pump therein that is fluidly coupled from a supply coupler on the control unit, through an umbilical tube assembly and a thermal body wrap, to a return coupler on the control unit, the apparatus further including a coolant heat exchange assembly that includes a coolant tank with a heat exchanger therein that is fluidly coupled to a thermal fluid inlet coupler and a thermal fluid outlet coupler, both disposed on an exterior surface of the coolant tank, and wherein the heat exchanger includes a first heat exchanger molding portion and a second heat exchanger molding portion, which are cooperatively formed to define opposing halves of plural heat exchange tubes and opposing halves of an inlet manifold and an outlet manifold, the method comprising the steps of:
joining together, in clamshell fashion, the first heat exchanger molding portion and a second heat exchanger molding portion, thereby defining plural heat exchange tubes, and defining an inlet manifold and an outlet manifold that are are fluidly coupled to the thermal fluid inlet coupler and said thermal fluid outlet coupler, respectively;
filling the coolant tank with a coolant, thereby immersing the heat exchanger in the coolant;
placing the coolant heat exchange assembly in a cold environment, thereby removing heat from the coolant that is in the coolant tank;
removing the coolant tank assembly from the cold environment;
coupling the control unit supply coupler and return coupler with the heat exchange assembly thermal fluid outlet coupler and the thermal fluid inlet coupler, respectively;
filling the heat exchanger, pump, umbilical tube assembly, and thermal body wrap with a thermal fluid;
engaging the thermal body wrap with a body from which heat is to be removed;
operating the pump, thereby circulating the thermal fluid between the thermal body wrap and the heat exchanger, and circulating within and through the heat exchange tubes, passing through the pump, the umbilical tube assembly, the supply coupler, the return coupler, the thermal fluid inlet coupler and the thermal fluid outlet coupler, thereby enabling the thermal fluid to transfer heat from the body to the coolant.

17. The method of claim 16, and further comprising the step of:
placing the coolant heat exchange assembly into an insulated enclosure, which has an opening for receiving the coolant heat exchange assembly, while engaged with the control unit, thereby substantially insulating the coolant heat exchange assembly against the coupling of external heat thereinto.

18. The method of claim 16, and wherein the coolant tank includes a first coolant tank portion and a second coolant tank portion, which are located on opposing sides of the heat exchanger, and contain a first portion of the coolant and a second portion of the coolant, respectively, and thereby thermally exposing the heat exchanger on opposing sides thereof to both of the first coolant portion and the second coolant portion.

19. The method of claim 16, and wherein the first heat exchanger molding portion, and the second heat exchanger molding portion are formed from thermoplastic.

20. The method of claim 16, and wherein the coolant is water mixed with an additive to prevent freezing above a temperature of minus twenty-five degrees Fahrenheit, and wherein the thermal fluid is selected from a mixture of water and isopropyl alcohol or propylene glycol, which mixture prevents freezing above a temperature of minus twenty-five degrees Fahrenheit.

21. The method of claim 16, and wherein the supply coupler, the return coupler, the thermal fluid inlet coupler and the thermal fluid outlet coupler are quick-connect tubing couplers having automatic shut-off valves therein to prevent the thermal fluid from leaking when disconnected.

* * * * *